| United States Patent [19] | [11] Patent Number: 4,496,649 |
|---|---|
| Leppard et al. | [45] Date of Patent: Jan. 29, 1985 |

[54] COLOR-PHOTOGRAPHIC RECORDING MATERIAL

[75] Inventors: David G. Leppard, Marly; Jean Rody, Riehen, both of Switzerland

[73] Assignee: Ciba-Geigy AG, Basel, Switzerland

[21] Appl. No.: 562,189

[22] Filed: Dec. 15, 1983

[30] Foreign Application Priority Data

Dec. 16, 1982 [CH] Switzerland ............... 7315/82

[51] Int. Cl.$^3$ ............... G03C 7/40; G03C 7/26
[52] U.S. Cl. ............... 430/372; 430/512; 430/523; 430/551; 430/931; 430/961
[58] Field of Search ............... 430/372, 505, 512, 523, 430/551, 931, 961

[56] References Cited

U.S. PATENT DOCUMENTS

| 3,993,655 | 11/1976 | Rasberger et al. | 260/293.64 |
| 4,148,783 | 4/1979 | Rasberger et al. | 546/16 |
| 4,198,334 | 4/1980 | Rasberger | 524/103 |
| 4,226,999 | 10/1980 | Malherbe et al. | 546/207 |
| 4,268,593 | 5/1981 | Leppard et al. | 430/512 |
| 4,452,884 | 6/1984 | Leppard | 430/551 |

FOREIGN PATENT DOCUMENTS

1326889  8/1973  United Kingdom .

*Primary Examiner*—J. Travis Brown
*Attorney, Agent, or Firm*—Wenderoth, Lind & Ponack

[57] ABSTRACT

A color-photographic recording material which, in at least one light-sensitive silver halide emulsion layer, an interlayer and/or a protective layer, contains at least one polyalkylpiperidine compound of the formula I $$R_1 \underset{R_2}{\overset{R}{\bigodot}} C(C_nH_{2n})A(CO-Y-X)_m \quad (I)$$

in which R is an OH group and $R_1$ is a group of the formula II $$M \underset{R_2}{\overset{R}{\bigodot}} C(C_nH_{2n})A(CO-Y-X)_m \quad (II)$$

or of the formula $$-C(C_nH_{2n})A(CO-Y-X)_m \quad (III)$$

and X is a group of the formula $$(CH_2)_a(CH)_b(CH_2)_c(Z)_d W \quad \underset{R_{10}}{\overset{R_6\ CH_3\ \ CH_2R_6}{\diagup\diagdown}} N-R_7$$

or of the formula $$-CH-CH_2-N \underset{R_{10}}{\overset{R_6CH_2\ \ CH_3\ R_6}{\diagup\diagdown}} \underset{R_6CH_2\ \ CH_3}{\overset{R_{11}}{\diagdown\diagup}} H$$

Color images obtained by imagewise exposure and development of this color-photographic recording material show good stability to the action of visible and ultraviolet light.

With respect to the definitions of the substituents and symbols in the formulae, reference is made to the description.

24 Claims, No Drawings

COLOR-PHOTOGRAPHIC RECORDING MATERIAL

The present application relates to a colour-photographic recording material which, in at least one light-sensitive silver halide emulsion layer and/or in at least one of the conventional auxiliary layers, contains a specific polyalkylpiperidine compound as a stabiliser.

As sterically hindered amines, polyalkylpiperidines are generally known as light stabilisers for organic materials, in particular for polymers. In German Offenlegungsschrift 2,126,954, the use of such polyalkylpiperidines as agents to counteract the fading of colour photographs was proposed in the past. Furthermore, EP-A 11,051 proposed the use of certain polyalkylpiperidine derivatives, which contain at least one phenol group, as light stabilisers for colour photographs. These are polyalkylpiperidine esters of hydroxybenzylmalonic acids.

It has now been found that polyalkylpiperidine compounds which contain a sterically hindered phenol linked via a carboxyalkylidene group or carbaminoalkylidene group exert a surprisingly improved stabilising action.

The subject of the present invention is therefore a colour-photographic recording material which, in at least one light-sensitive silver halide emulsion layer, an interlayer and/or a protective layer, contains at least one polyalkylpiperidine compound as a stabiliser, wherein the polyalkylpiperidine compound is of the formula I

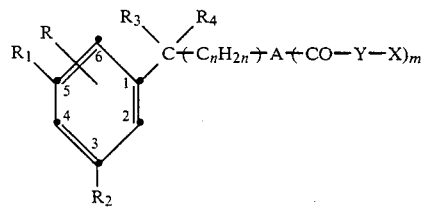

in which R is an OH group in the 2-position, 4-position or 6-position, $R_1$ is hydrogen, $C_1$–$C_4$-alkyl, a group of the formula II

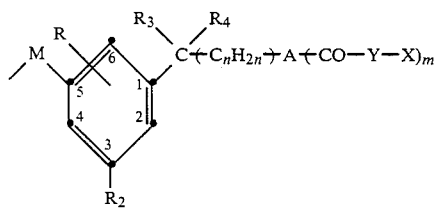

or a group of the formula III

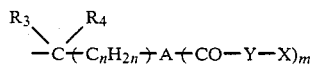

$R_2$ is $C_1$–$C_4$-alkyl, a group of the formula III or a group of the formula —CO—Y—X, $R_3$ and $R_4$ independently of one another are $C_1$–$C_8$-alkyl and, in addition, $R_4$ can, together with the group —($C_nH_{2n}$)—, form a $C_5$–$C_{12}$-cycloalkyl radical, n is a number from 1 to 20, m is 1 or 2, A is a direct C—C bond if m=1 or a radical

if m=2, Y is —O— or N($R_5$)—, wherein $R_5$ is hydrogen, $C_1$–$C_{18}$-alkyl, $C_3$–$C_{12}$-alkenyl, $C_3$–$C_{12}$-cycloalkyl, phenyl, $C_7$–$C_{14}$-aralkyl, $C_7$–$C_{14}$-alkaryl, $C_2$–$C_{11}$-alkoxyalkyl or a group of the formula IV

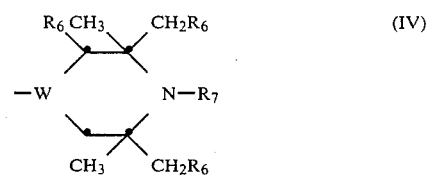

M is a direct bond, —O—, —S—, —S—S—, —SO—, —$SO_2$— or a group —$CH_2OCH_2$—, —$CH_2SCH_2$—, —CH($R_8$)— or —N($R_9$)—, wherein $R_8$ is hydrogen, $C_1$–$C_{12}$-alkyl or $C_3$–$C_8$-alkyl interrupted by 1–3 sulfur atoms and $R_9$ is hydrogen, $C_1$–$C_{18}$-alkyl or unsubstituted or $C_1$–$C_4$-alkyl-substituted phenyl or benzyl, X is a group of the formula

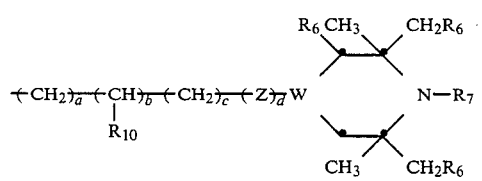

or of the formula

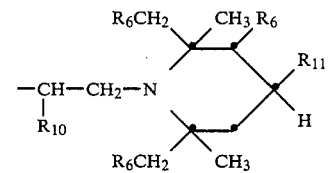

a is one of the numbers from 0 to 10, b, c and d independently of one another are the number 0 or 1, it being necessary for the sum a+b+c≠0 if d=1, $R_6$ is hydrogen or methyl, $R_7$ is hydroxyl, $C_1$–$C_{12}$-alkyl, $C_3$–$C_6$-alkenylmethyl, $C_3$–$C_4$-alkynylmethyl, $C_7$–$C_{14}$-aralkyl, glycidyl, $C_1$–$C_4$-alkyl substituted by halogen, cyano, —$COOR_{12}$ or —$CON(R_{13})(R_{14})$, a group —$COR_{15}$, —$COOR_{12}$, —$CON(R_{13})(R_{14})$, —$CH_2$—$CH(R_{16})$—$OR_{17}$, —$SOR_{18}$, —$SO_2R_{18}$, —$OR_{12}$ or —$OCOR_{15}$, $R_{12}$ being $C_1$–$C_{12}$-alkyl, allyl, cyclohexyl or benzyl, $R_{13}$ being $C_1$–$C_{12}$-alkyl, allyl, cyclohexyl, benzyl, phenyl or $C_7$–$C_{10}$-alkylphenyl, $R_{14}$ being hydrogen, $C_1$–$C_{12}$-alkyl, allyl, cyclohexyl or benzyl, or $R_{13}$ and $R_{14}$, together with the N atom to which they are attached, forming a 5-membered or 6-membered heterocyclic ring, $R_{15}$ being hydrogen, $C_1$–$C_{12}$-alkyl, $C_2$–$C_6$-alkenyl, chloromethyl, $C_5$–$C_8$-alkyl, $C_7$–$C_{14}$-aralkyl, phenyl, $C_7$–$C_{10}$-alkylphenyl or phenyl, phenylmethyl or phenylethyl which are substituted by 1 or 2 $C_1$–$C_4$-alkyls and 1 hydroxyl, $R_{16}$ being hydrogen, $C_1$–$C_4$-alkyl, $C_3$–$C_4$-alkoxyalkyl, phenyl or phenoxymethyl, $R_{17}$ being hydrogen, $C_1$–$C_{12}$-alkyl, a group —$COR_{15}$ or —$CON(R_{13})(R_{14})$ or a group of the formula

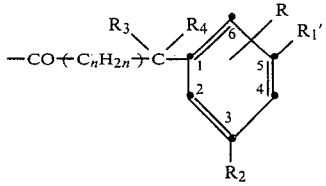

in which $R_1'$ is hydrogen or $C_1$-$C_4$-alkyl, and $R_{18}$ being $C_1$-$C_{12}$-alkyl, phenyl or $C_7$-$C_{10}$-alkylphenyl, or $R_7$ is a group of the formula

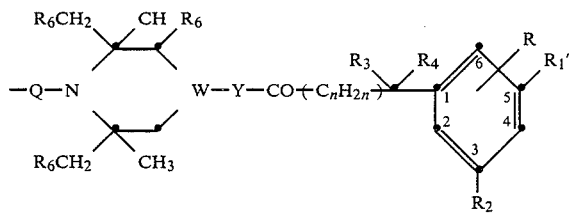

in which Q is —$(C_rH_{2r})$— wherein r is one of the numbers 2 to 12, or Q is $C_4$-$C_8$-alkenylene, $C_5$-$C_{12}$-cycloalkylene, phenylene, xylylene, bitolylene or a group —CO—$(C_rH_{2r})$—CO—, Z is —O— or —N($R_{19}$)— wherein $R_{19}$ is hydrogen, $C_1$-$C_{18}$-alkyl, $C_3$-$C_{12}$-alkenyl, $C_3$-$C_{12}$-cycloalkyl, phenyl, $C_7$-$C_{14}$-alkaryl, $C_7$-$C_{14}$-aralkyl, $C_2$-$C_{11}$-alkoxyalkyl or a group —$COR_{20}$, —$COOR_{21}$, —$CON(R_{22})(R_{23})$, —$CH_2$—$CH(R_{24})$—$OR_{25}$, —$SOR_{26}$ or —$SO_2R_{26}$, $R_{20}$ having one of the meanings defined for $R_{15}$ or being a heterocyclic ring, $R_{21}$ having one of the meanings defined for $R_{12}$, $R_{22}$ having one of the meanings defined for $R_{13}$, $R_{23}$ having one of the meanings defined for $R_{14}$, $R_{24}$ having one of the meanings defined for $R_{16}$, $R_{25}$ having one of the meanings defined for $R_{17}$ and $R_{26}$ having one of the meanings defined for $R_{18}$, or $R_{19}$ is a group of the formula IV, $R_{10}$ is hydrogen, $C_1$-$C_{18}$-alkyl, $C_7$-$C_{23}$-phenoxyalkyl, phenyl, $C_7$-$C_{14}$-aralkyl, $C_2$-$C_{11}$-alkoxyalkyl or a group

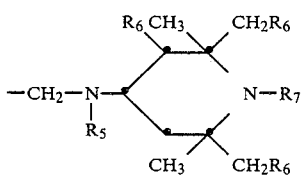

$R_{11}$ is hydrogen, —$OR_{27}$, —$OCOR_{28}$, —$N(R_{29})$—$COR_{28}$, —$OSO_2R_{28}$ and —$N(R_{29})$—$SO_2R_{28}$, $R_{27}$ being hydrogen, $C_1$-$C_{12}$-alkyl, allyl or benzyl, $R_{28}$ being hydrogen, $C_1$-$C_{12}$-alkyl, $C_2$-$C_6$-alkenyl, chloromethyl, $C_5$-$C_8$-cycloalkyl, $C_7$-$C_9$-phenylalkyl, $C_7$-$C_{10}$-alkylphenyl, phenyl or a group of the formula

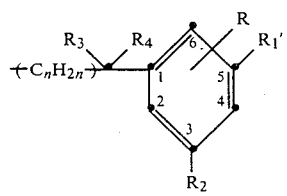

and $R_{29}$ being hydrogen, $C_1$-$C_{12}$-alkyl, $C_5$-$C_8$-cycloalkyl or benzyl, and W being one of the groups

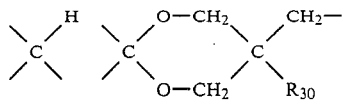

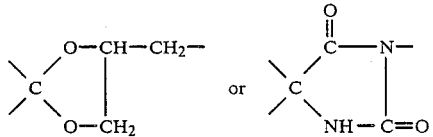

in which $R_{30}$ is methyl or ethyl, with the proviso that, if W is a cyclic ketal structure, d is 0 and the sum $a+b+c$ must also be 0 and, if W is a hydantoin structure, d must be 0 and the sum $a+b+c$ must be $\neq 0$, the repeatedly mentioned radicals and symbols always being as defined in the first instance and, with repeated occurrence of the group

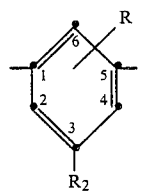

R always being in the same position.

Any alkyl substituents are straight-chain or branched alkyl groups. $C_1$-$C_4$-alkyl groups are methyl, ethyl, n-propyl, isopropyl, n-butyl, sec.-butyl or tert.-butyl. $C_1$-$C_8$-alkyl groups also include, for example, n-pentyl, 2,2-dimethylpropyl, n-hexyl, 2,3-dimethylbutyl, n-octyl and 1,1,3,3-tetramethylbutyl. $C_1$-$C_{12}$-Alkyl groups also include, for example, nonyl, decyl, undecyl and dodecyl. $C_1$-$C_{18}$-alkyl groups also include, for example, tetradecyl, hexadecyl, heptadecyl and octadecyl.

Any $C_5$-$C_8$-cycloalkyl substituents are, for example, cyclopentyl, cyclohexyl, cycloheptyl, α-methylcyclohexyl, cyclooctyl or dimethylcyclohexyl. $C_3$-$C_{12}$-cycloalkyl groups also include, for example, cyclopropyl, cyclononyl, cyclodecyl and cyclododecyl. Cyclohexyl is preferred.

Examples of $C_7$-$C_9$-phenylalkyl groups $R_{28}$ are benzyl, phenylethyl and phenylpropyl. Any $C_7$-$C_{14}$-aralkyl substituents also include, for example, phenylbutyl and naphthylmethyl.

Any $C_7$-$C_{10}$-alkylphenyl substituents are, for example, tolyl, xylyl, isopropylphenyl, tert.-butylphenyl and diethylphenyl.

Examples of $C_3$-$C_6$-alkenylmethyl groups $R_7$ are allyl, methallyl, dimethylallyl and 2-hexenyl. $C_2$-$C_6$-alkenyl groups $R_{15}$ and $R_{28}$ can also be vinyl.

Examples of $C_3$-$C_{12}$-alkenyl groups $R_5$ and $R_{19}$ are allyl, methallyl, 2-butenyl, 2-hexenyl, 2-octenyl, 4-octenyl, 2-decenyl and 2-dodecenyl. Allyl is preferred.

$C_3$-$C_4$-alkynylmethyl groups $R_7$ are, for example, propargyl, n-but-1-ynyl or n-but-2-ynyl. Propargyl is preferred.

Any $C_7$-$C_{14}$-alkaryl substituents are, for example, $C_1$-$C_4$-alkyl-substituted phenyl, such as p-tolyl, 2,4-dimethylphenyl, 2,6-dimethylphenyl, 2,4-diethylphenyl, 2,6-diethylphenyl, 4-tert.-butylphenyl, 2,4-di-tert.- butylphenyl or 2,6-di-tert.-butylphenyl. 2,4-Di-tert.-butylphenyl and 2,4-dimethylphenyl are preferred.

A heterocyclic ring $R_{15}$ is, for example, pyrrole, pyridine, indole, quinoline, pyrrolidine, thiophene, furan, imidazole, pyrazine, pyrimidine, thiazole, oxazole, piperazine, morpholine or piperidine.

$C_3-C_4$-alkoxyalkyl groups $R_{16}$ are, for example, ethoxymethyl, 2-methoxyethyl or 2-ethoxyethyl. $C_2-C_{11}$-alkoxyalkyl groups $R_5$, $R_{10}$ and $R_{19}$ also include methoxymethyl, 2-n-butoxyethyl, 2-n-butoxypropyl, 2-n-octoxyethyl, 3-n-octoxypropl and 6-n-butoxyphenyl.

Examples of $C_7-C_{23}$-phenoxyalkyl groups $R_{10}$ are phenoxymethyl, phenoxyethyl, phenoxypropyl, phenoxybutyl, phenoxyoctyl, phenoxydecyl, phenoxydodecyl and phenoxyhexadecyl.

Any halogen substituents are, for example, bromine, iodine or especially chlorine.

In the group —$C_nH_{2n}$— with n a number between 1 and 20, n is preferably a number between 2 and 8 and especially 3. Examples are methylene, ethylene, trimethylene, tetramethylene, hexamethylene, octamethylene, nonamethylene, 2,2,4-trimethylhexamethylene, decamethylene and dodecamethylene.

Phenyl, phenylmethyl or phenylethyl groups $R_{15}$ and $R_{20}$ which are substituted by 1 or 2 $C_1-C_4$-alkyls and 1 hydroxyl are, for example, 2,5-dimethyl-4-hydroxyphenyl, 3,5-di-tert.-butyl-4-hydroxyphenyl, 3,5-dimethyl-4-hydroxybenzyl, 3,5-di-tert.-butyl-4-hydroxybenzyl or 2-(3,5-di-tert.-butyl-4-hydroxyphenyl)-ethyl.

Those colour-photographic recording materials are preferred which, as stabilisers, contain at least one compound of the formula Ia

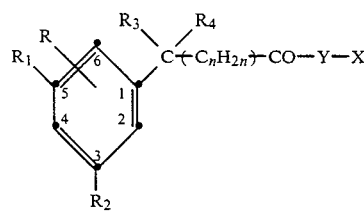

in which the substituents R, $R_1$, $R_2$, $R_3$, $R_4$, Y and X as well as the index n are as already defined above.

Those colour-photographic recording materials are preferred which, as the stabiliser, contain at least one compound of the formula V

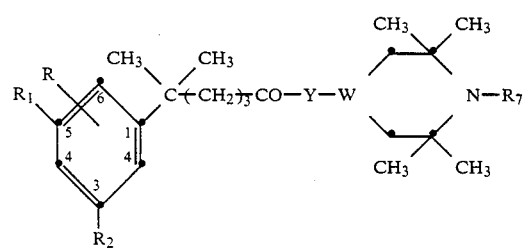

in which R is an OH group in the 2-position, 4-position or 6-position, $R_1$ is hydrogen, $C_1-C_4$-alkyl, a group of the formula VI

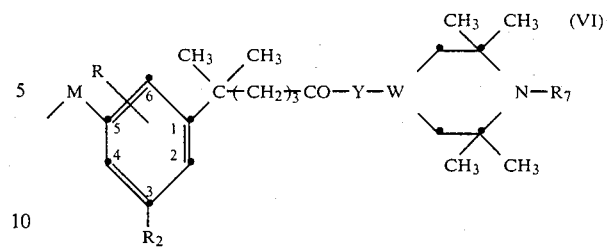

or a group of the formula VII

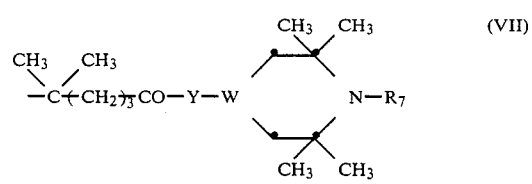

$R_2$ is $C_1-C_4$-alkyl or a group of the formula VII, Y is —O— or —N($R_5$)—, $R_5$ being hydrogen, $C_1-C_{12}$-alkyl, cyclohexyl, $C_3-C_4$-alkoxyalkyl or a group of the formula VIII

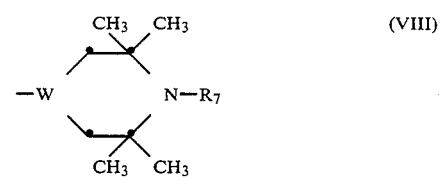

M is —CH($R_8$)— or —S—, $R_8$ being hydrogen or $C_1-C_4$-alkyl, $R_7$ is hydroxyl, methyl, allyl, benzyl, 2-hydroxyethyl, acetyl, acroyl or a group —CON($R_{13}$)($R_{14}$), wherein $R_{13}$ is $C_1-C_8$-alkyl, cyclohexyl or phenyl and $R_{14}$ is hydrogen, $C_1-C_8$-alkyl or cyclohexyl, or $R_7$ is a group of the formula

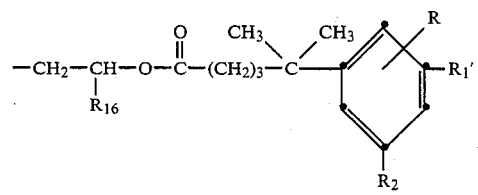

in which $R_{16}$ is hydrogen or methyl, and W is one of the groups

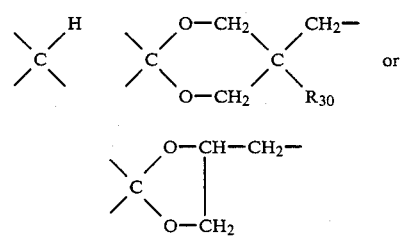

in which $R_{30}$ is methyl or ethyl, the radicals mentioned repeatedly under this preferred formula always being as defined in the first instance under this preferred formula and, with repeated occurrence of the group

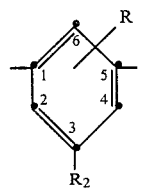

R always being in the same position.

Those colour-photographic recording materials are particularly preferred which, as the stabiliser, contain at least one compound of the formula IX

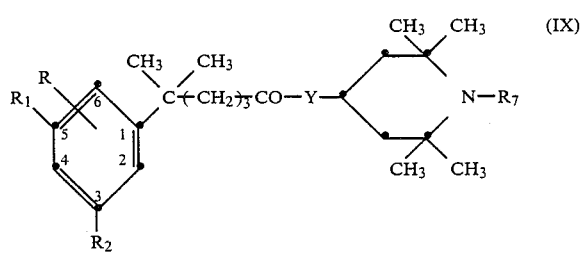

in which R is an OH group in the 2-position, 4-position or 6-position, $R_1$ is hydrogen, $C_1$-$C_4$-alkyl or a group of the formula X

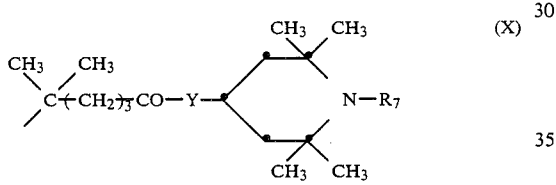

$R_2$ is $C_1$-$C_4$-alkyl or a group of the formula X, Y is —O— or —N($R_5$)—, wherein $R_5$ is hydrogen or $C_1$-$C_8$-alkyl, and $R_7$ is hydroxyl, methyl, allyl, benzyl, 2-hydroxyethyl, acetyl, acryloyl or a group of the formula

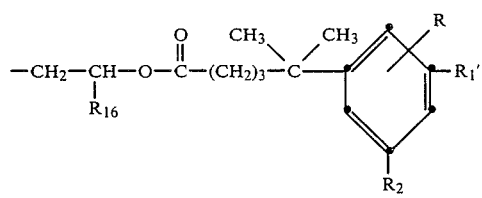

in which $R_{16}$ is hydrogen or methyl.

Furthermore, those colour-photographic recording materials are preferred which, as the stabiliser, contain at least one compound of the formula I or of the formula V or of the formula IX, wherein the radical R is in the 2-position or in the 4-position or in the 6-position.

The compounds of the formula I are novel and as such are likewise a subject of the present invention.

They can be obtained analogously to known compounds, for example those described in German Offenlegungsschriften 2,456,864, 2,647,452, 2,654,058 and 2,656,769. The last stage of the synthesis is either a direct esterification (acid+alcohol or acid chloride+alcohol), a transesterification or an amidation. The polyalkylpiperidine compounds used as the starting material for the preparation of the compounds of the formula I are known. If some of these should still be novel, they can be obtained analogously to the known compounds.

The sterically hindered phenol derivatives used as starting materials are novel. These are phenols of the formula XI

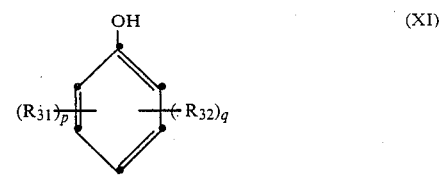

in which p is one of the numbers 1, 2 and 3 and q is one of the numbers 0, 1 and 2, with the proviso that $p+q \leq 3$, $R_{31}$ is a group of the formula XII

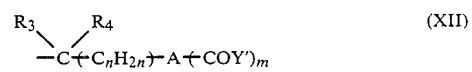

in which $R_3$, $R_4$, A, m and n are as defined above and Y' is —OR' or —N($R_5$)H, R' being hydrogen, methyl or ethyl and $R_5$ being as defined above, and $R_{32}$ is $C_1$-$C_4$-alkyl or one of the groups

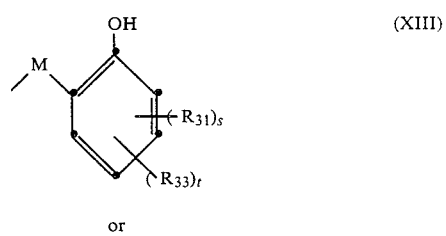

or

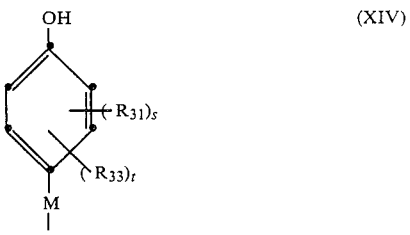

in the 2-position, 4-position or 6-position relative to the OH group, wherein M and $R_{31}$ are as defined above, $R_{33}$ is $C_1$-$C_4$-alkyl, s is one of the numbers 0, 1 and 2, and t is one of the numbers 0 and 1, with the proviso that $s+t \leq 2$, not more than one group of the formula XIII or XIV being present in the phenol of the formula XI; and provided furthermore that, if n is 1 or 2 and R' is hydrogen, then m must be 2.

The phenols of the formula XI can be prepared by reacting a phenol of the formula XV

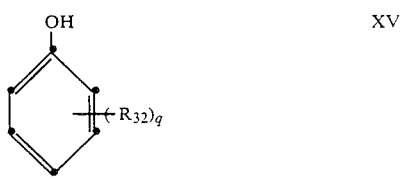

in which $R_{32}$ and q are as defined above, and with the proviso that a group of the formula XIII or XIV must not be present more than once in the formula XV and must be in the 2-position, 4-position or 6-position relative to the OH group, with a functional alkylating agent (XXI) which is capable of introducing a group of the formula XII, in the presence of a suitable catalyst.

The alkylation takes place at temperatures between 20 and 170, preferably between 100° and 150° C. Suitable catalysts are Brönsted acids, active earths or metal salts. The Brönsted acids can be organic or inorganic acids or even partial salts thereof. For example, such an acid can be a mineral acid, such as hydrochloric acid, sulfuric acid, perchloric acid or orthophosphoric acid, or an inorganic acid substituted by alkyl, aryl or alkaryl, such as methanesulfonic acid, ethanesulfonic acid, benzenesulfonic acid, p-toluenesulfonic acid or methanephosphonic acid, or an organic acid, such as dichloroacetic acid, trichloroacetic acid or trifluoroacetic acid. Examples of suitable active earths are Fulmont 237 ® or Fulcat 22 ®, whilst aluminium phenoxide, for example, can be used as a metal salt. The active earths are preferred.

The reaction can be carried out with or without a solvent. Examples of suitable solvents are methanol/sulfuric acid or water/sulfuric acid. These solvents also act as catalysts. The compounds of the formula XI are obtained from compounds of the formula XV by reaction with 0.1 to 4.0 moles of the alkylating agent (XXI), depending on the meaning of p and q.

Typical representatives of the formula I are listed in Tables I to VI which follow.

TABLE I

[Structure: 2,6-di-tert-butyl-4-hydroxyphenyl group with $-C(CH_3)_2-(CH_2)_n-CO-Y-X$ substituent]

| Stabiliser No. | n | Y | X |
|---|---|---|---|
| 1 | 3 | —O— | 2,2,6,6-tetramethyl-piperidinyl, N—COCH₃ |
| 2 | 3 | —O— | 2,2,6,6-tetramethyl-piperidinyl, N—CH₃ |
| 3 | 3 | —O— | 2,2,6,6-tetramethyl-piperidinyl, N—CH₂—C₆H₅ |
| 4 | 3 | —O— | 2,2,6,6-tetramethyl-piperidinyl, N—CO—CH=CH₂ |
| 5 | 3 | —O— | 2,2,6,6-tetramethyl-piperidinyl, N—CON(C₂H₅)₂ |

TABLE I-continued
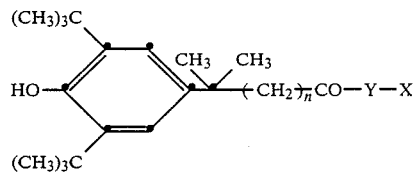
| Stabiliser No. | n | Y | X |
|---|---|---|---|
| 6 | 3 | —O— | 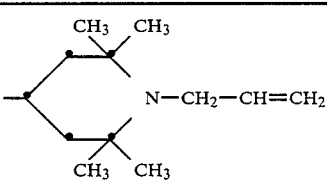 |
| 7 | 1 | —O— | 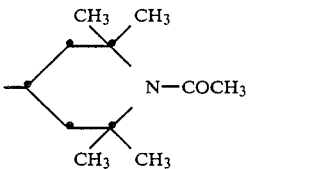 |
| 8 | 3 | —O— | 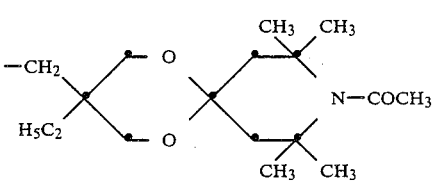 |
| 9 | 3 | —NH— | 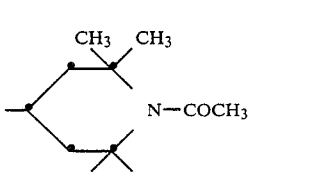 |
| 10 | 3 | —NH— | 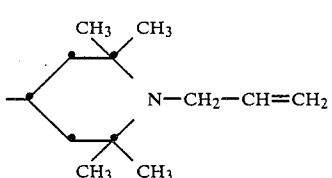 |
| 11 | 3 | —N(CH₃)— | 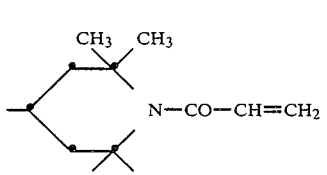 |
| 12 | 1 | —N(CH₃)— | 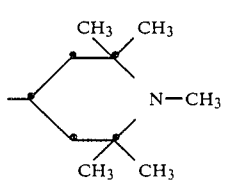 |

TABLE I-continued
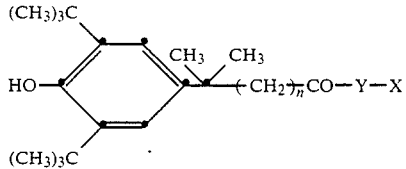
| Stabiliser No. | n | Y | X |
|---|---|---|---|
| 13 | 3 | 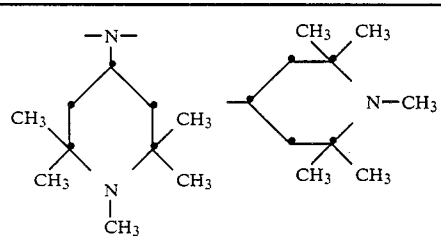 | 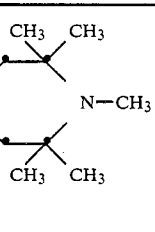 |
TABLE II
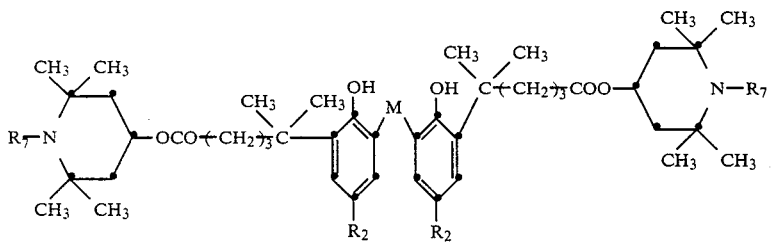
| Stabiliser No. | M | $R_2$ | $R_7$ |
|---|---|---|---|
| 14 | $-CH_2-$ | $-CH_3$ | $-COCH_3$ |
| 15 | $-CH_2-$ | $-C(CH_3)_3$ | $-COCH_3$ |
| 16 | $-CH_2-$ | $-CH_3$ | $-CO-CH=CH_2$ |
| 17 | $-CH_2-$ | $-CH_3$ | $-CH_3$ |
| 18 | $-CH_2-$ | $-CH_3$ | 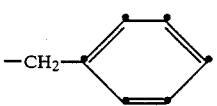 |
| 19 | $-S-$ | $-C(CH_3)_3$ | $-COCH_3$ |
| 20 | $-S-$ | $-CH_3$ | $-CH_3$ |
| 21 | $-S-$ | $-CH_3$ | 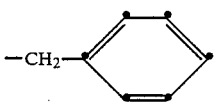 |
| 22 | $-S-$ | $-C(CH_3)_3$ | $-CO-CH=CH_2$ |

TABLE III

[Structure: piperidine-OCO-(CH2)3-C(CH3)2-CH(CH3)-[phenol with R2, OH]-M-[phenol with OH, R2]-CH(CH3)-C(CH3)2-(CH2)3-OCO-piperidine, with N-R7 on piperidines]

| Stabiliser No. | M | $R_2$ | $R_7$ |
|---|---|---|---|
| 23 | — | $-C(CH_3)_3$ | $-CH_3$ |
| 24 | — | $-C(CH_3)_3$ | $-COCH_3$ |
| 25 | $-CH_2-$ | $-C(CH_3)_3$ | $-CH_2-C_6H_5$ |
| 26 | $-S-$ | $-C(CH_3)_3$ | $-CH_3$ |

TABLE IV

[Structure: piperidine-OCO-(CH2)3-C(CH3)2-[phenol with R2, HO]-M-[phenol with R2, OH]-C(CH3)2-(CH2)3-OCO-piperidine, with N-R7 on piperidines]

| Stabiliser No. | M | $R_2$ | $R_7$ |
|---|---|---|---|
| 27 | — | $-C(CH_3)_3$ | $-COCH_3$ |
| 28 | $-CH_2-$ | $-CH_3$ | $-CO-CH=CH_2$ |
| 29 | $-S-$ | $-C(CH_3)_3$ | $-COCH_3$ |

TABLE V

[Structure: phenol with OH, R1, R2 substituents; C(CH3)2-(CH2)3-COO-piperidine with N-R7]

| Stabiliser No. | $R_1$ | $R_2$ | $R_7$ |
|---|---|---|---|
| 30 | $-C(CH_3)_2-(CH_2)_3-COO-$piperidinyl-$N-R_7$ | $-C(CH_3)_2-(CH_2)_3-COO-$piperidinyl-$N-R_7$ | $-COCH_3$ |

TABLE V-continued

[Structure: 2-hydroxyphenyl with R1 at position 3, R2 at position 5, and a -C(CH3)2-(CH2)3-COO- linker to a 2,2,6,6-tetramethylpiperidine with N-R7]

| Stabiliser No. | R₁ | R₂ | R₇ |
|---|---|---|---|
| 31 | -C(CH₃)₂-(CH₂)₃-COO-[2,2,6,6-tetramethylpiperidine-N-R₇] | -C(CH₃)₂-(CH₂)₃-COO-[2,2,6,6-tetramethylpiperidine-N-R₇] | -CH₂-C₆H₅ |
| 32 | -C(CH₃)₂-(CH₂)₃-COO-[2,2,6,6-tetramethylpiperidine-N-R₇] | -CH₃ | -COCH₃ |
| 33 | -H | -C(CH₃)₃ | -CO-CH=CH₂ |
| 34 | -C(CH₃)₃ | -C(CH₃)₃ | -COCH₃ |
| 35 | -C(CH₃)₃ | -C(CH₃)₃ | -CON(C₂H₅)₂ |

TABLE VI

[Structure: 2-hydroxyphenyl with R1 at position 3, R2 at position 5, and a -C(CH3)2-(CH2)3-COY-X substituent]

| Stabiliser No. | R₁ | R₂ | Y | X |
|---|---|---|---|---|
| 36 | -C(CH₃)₃ | -C(CH₃)₃ | -O- | -[2,2,6,6-tetramethylpiperidine-N]-CH₂-C₆H₄-CH₂-[N-2,2,6,6-tetramethylpiperidine]-O-CO-(CH₂)₂-[3,5-di-tert-butyl-4-hydroxyphenyl with C(CH₃)₂ linker] |
| 37 | -C(CH₃)₃ | -C(CH₃)₃ | -O- | -(CH₂)₂-N[2,2,6,6-tetramethylpiperidine] |
| 38 | -C(CH₃)₃ | -C(CH₃)₃ | -O- | -CH₂-C(C₂H₅)(CH₂-O-[2,2,6,6-tetramethylpiperidine-N-CO-CH=CH₂])₂ |

TABLE VI-continued
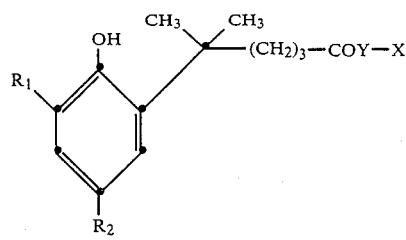
| Stabiliser No. | $R_1$ | $R_2$ | Y | X |
|---|---|---|---|---|
| 39 | —C(CH$_3$)$_3$ | —C(CH$_3$)$_3$ | —O— | (see structure below) |
structure for 39: piperidine-N—(CH$_2$)$_2$—O—CO—(CH$_2$)$_3$—C(CH$_3$)$_2$—[2,4-di-tert-butyl-6-hydroxyphenyl]
| 40 | H | —C(CH$_3$)$_3$ | —NH— | 2,2,6,6-tetramethyl-1-methyl-piperidin-4-yl |
The following are further typical representatives of compounds of the formula I:
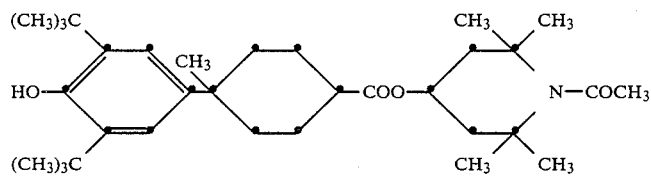
41.
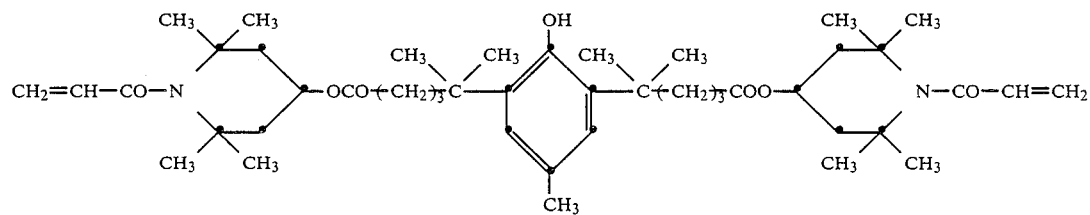
42.
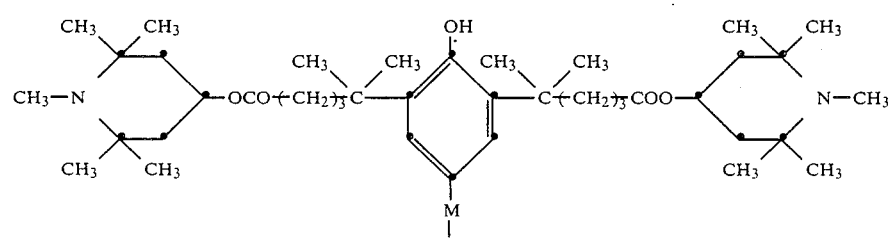

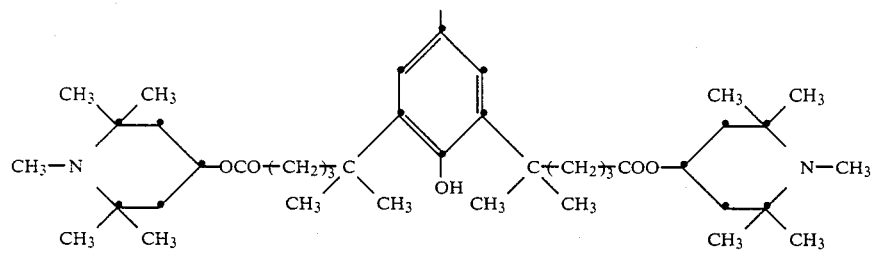
M = —CH$_2$— 43.
M = —S— 44.
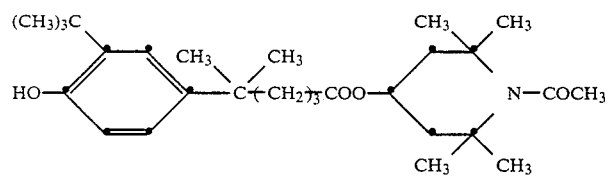 45.
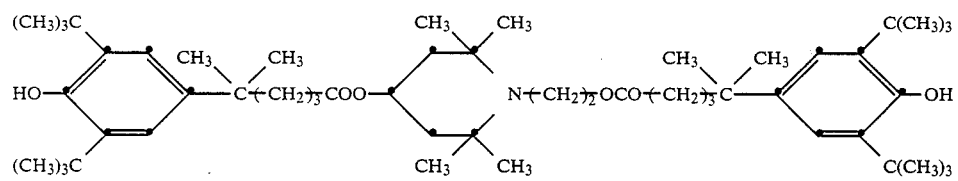 46.
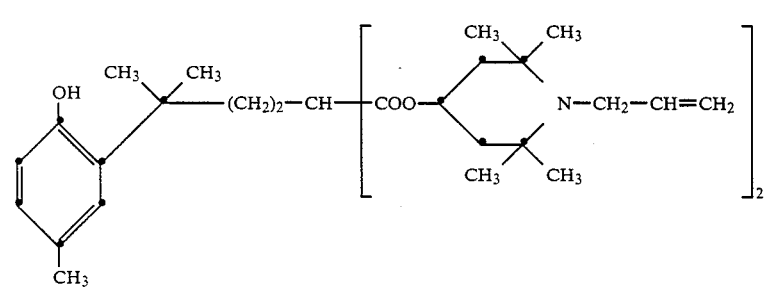 47.
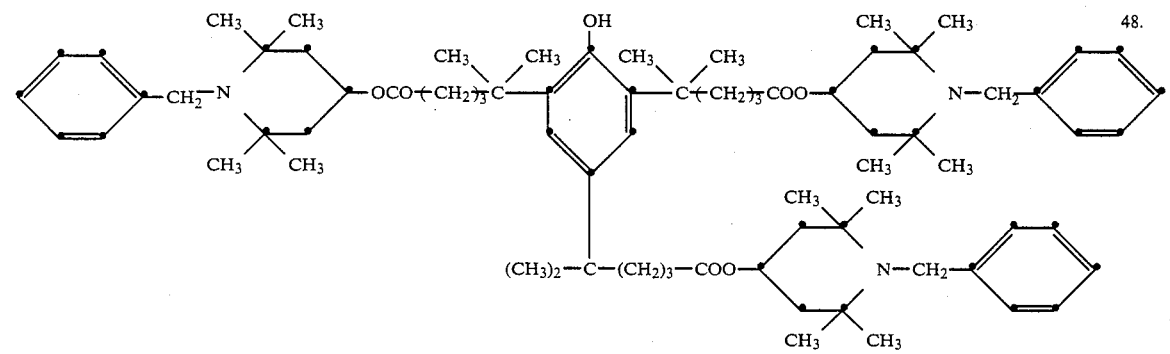 48.

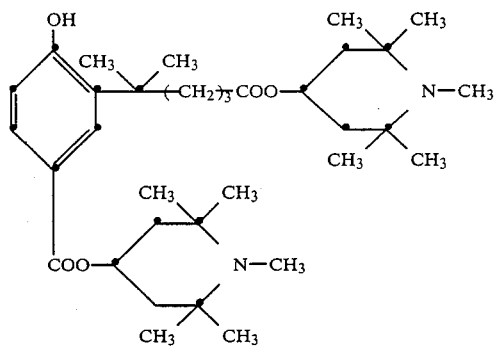

49.

The stabilizers of the formula I can be incorporated, by themselves or together with other compounds, in a known manner into a photographic material.

As a rule, the stabilisers are incorporated, by themselves or together with other compounds, in particular with colour couplers, in the form of a dispersion into the photographic material, this dispersion either containing no solvent or containing high-boiling or low-boiling solvents or a mixture of such solvents. In a further suitable incorporation method, the stabilisers are incorporated, by themselves or together with other compounds, together with a polymer in the form of a latex into the photographic material.

The dispersions are then used for preparing the layers of colour-photographic recording materials. These layers can be, for example, interlayers or protective layers, but in particular light-sensitive (blue-sensitive, green-sensitive and red-sensitive) silver halide emulsion layers in which, on development of the exposed recording material, the blue-green (cyan), purple (magenta) and yellow dyes are formed from the corresponding colour couplers.

The silver halide layers can contain any desired colour couplers, in particular cyan, magenta and yellow couplers, which are used for forming the said dyes and hence the colour images.

Since the substrate has an influence on the action and stability of the compounds of the formula I, those substrates (solvents, polymers) are preferred which, together with these stabilisers, result in the best possible stability of the materials which are to be stabilised.

As a rule, the stabilisers of the formula I are incorporated into layers which additionally contain a silver halide dispersion which has been prepared and sensitised by conventional methods. However, they can also be present in layers adjacent to the layers containing silver halide.

The photographic materials according to the invention have a conventional structure and contain conventional components. That structure and those components are, however, preferred which intensify the activity of the stabilisers of the formula I or at least do not affect it adversely.

In the photographic recording material according to the present invention, the stabilisers of the formula I can, apart from the colour couplers, additionally also be combined with ultraviolet absorbers or other light stabilisers in the same layer.

If the diffusion transfer method is used, the stabiliser can also be incorporated into a receiving layer.

The colour-photographic materials according to the invention can be processed in the known manner. Moreover, during or after processing, they can be treated in a way which further increases their stability, for example by treating in a stabiliser bath of by applying a protective coating.

The stabilisers to be used according to the invention are in certain cases also suitable for protecting colour-photographic layers in which the dyes are incorporated directly into the emulsion and the image is produced by selective bleaching.

The quantity of the stabiliser or stabilisers can vary within wide limits and is approximately in the range from 1 to 2,000 mg, preferably 100 to 800 and in particular 200–500 mg, per $m^2$ of the layer into which it or they is or are being incorporated.

If the photographic material contains an agent which absorbs ultraviolet radiation, this agent can be present together with the stabiliser in one layer, or even in an adjacent layer. The quantity of ultraviolet absorber or absorbers can vary within wide limits and is approximately in the range from 200 to 2,000 mg, preferably 400 to 1,000 mg, per $m^2$ of the layer in which it or they is or are incorporated. Examples of ultraviolet absorbers are compounds of the benzophenone, acrylonitrile, thiazolidone, benzotriazole, oxazole, thiazole and imidazole types.

The colour images obtained by exposure and development using the recording material according to the invention show very good lightfastness to visible and ultraviolet light. The compounds of the formula I are virtually colourless, so that there is no discolouration of the images; furthermore, they are highly compatible with the conventional photographic additives present in the individual layers. Due to their high activity, the quantity in which they are used can be reduced, and they are thus prevented from precipitating or crystallising out, when they are incorporated as an organic solution into the aqueous binder emulsions which are used for the preparation of photographic layers. The individual processing steps necessary for the production of the colour images after the exposure of the photographic recording material are not adversely affected by the stabilisers of the formula I. Moreover, the so-called abrasion fog which frequently occurs with blue-sensitive emulsions can be largely suppressed. This can occur, for example, when mechanical stresses, for example twisting, bending or rubbing, are exerted on photographic materials (silver halide emulsion layers located on a base of natural or synthetic materials), during production or during the treatment before development (T. H. James, The Theory of Photographic Process, 4th edition, Macmillan, New York, N.Y. 1977, pages 23 et seq, and pages 166 et seq.).

The examples which follow serve to explain the invention in more detail. Parts therein are parts by weight.

PREPARATION OF THE PHENOLIC STARTING MATERIALS

Example 1

94 parts of phenol, 14.2 parts of methyl 5-methylhex-5-enoate and 5.0 parts of Fulmont 237 ® are stirred for 20 hours at 110° C. After partial cooling of the reaction mixture, the catalyst is filtered off. After 82 parts of phenol have been separated off, this gives methyl 5-(4-hydroxyphenyl)-5-methyl-hexanoate with a boiling point of 167°–72° C./O, 65 mbar.

| Analysis for $C_4H_{20}O_3$ | | |
|---|---|---|
| | C | H |
| Found | 71.01% | 8.60% |
| Calculated | 71.16% | 8.83% |

Repeating Example 1 under the conditions indicated in Table VII which follows, the sterically hindered phenols listed in Table VII are obtained.

TABLE VII

| Example No. | Phenol (parts) | Alkylating agent (parts) | Catalyst (parts) | Reaction temperature in °C. | Reaction time in hours | End product |
|---|---|---|---|---|---|---|
| 2 | phenol (94) | $CH_3-\langle\text{cyclohexenyl}\rangle-COOCH_3$ (30,8) | Al(OPh)₃ from Al(0.3) | 175 | 40 | 2-substituted methyl hydroxyphenyl ester |
| 3 | phenol (37,8) | $CH_2=C(CH_3)(CH_2)_3COOCH_3$ (28,4) | Fulmont 237 ® (5.0) | 125 | 20 | 2,4-bis-substituted phenol |
| 4 | o-cresol (108) | $CH_2=C(CH_3)(CH_2)_3COOCH_3$ (56.8) | Fulmont 237 ® (5.0) | 125 | 24 | 3-methyl-4-substituted phenol |
| 5 | p-cresol (108) | $CH_2=C(CH_3)(CH_2)_3COOCH_3$ (56.8) | Fulmont 237 ® (5,0) | 150 | 20 | 4-methyl-2-substituted phenol |
| 6 | 2,6-dimethylphenol (122) | $CH_2=C(CH_3)(CH_2)_3COOCH_3$ (28.4) | Fulmont 237 ® (10) | 120 | 24 | 3,5-dimethyl-4-substituted phenol |
| 7 | 2,4-dimethylphenol (122) | $CH_2=C(CH_3)(CH_2)_3COOCH_3$ (28.4) | Fulmont 237 ® (10) | 120 | 24 | 3,5-dimethyl-2-substituted phenol |
| 8 | 4-tert-butylphenol (75) | $CH_2=C(CH_3)(CH_2)_3COOCH_3$ (28.4) | Fulmont 237 ® (5,0) | 125 | 20 | 4-tert-butyl-2-substituted phenol |

Example 9

12.5 parts of methyl 5-(2-hydroxy-5-methylphenyl)-5-methylhexanoate (prepared according to Example 5), 14.2 parts of methyl 5-methyl-hex-5-enoate and 1.0 part of p-toluenesulfonic acid are heated for 8 days on a steam bath. The reaction mixture is then diluted with ether, washed with 2N sodium hydroxide solution and then with water and finally evaporated. After distillation of the remaining oil in vacuo and after recrystallisation of the distillate from petroleum ether, bis-2,6-(5-methoxycarbonyl-2-methyl-pent-2-yl)-4-methylphenol of melting point 55°–57° C. is obtained.

| Analysis for $C_{23}H_{36}O_5$ | | |
|---|---|---|
| | C | H |
| Calculated | 70.25% | 9.01% |
| Found | 70.38% | 9.24% |

PREPARATION OF THE STABILISERS OF THE FORMULA I, TO BE USED ACCORDING TO THE INVENTION

By transesterifying the end products from Examples 1 to 9 by conventional methods with the polyalkyl-piperidine compounds

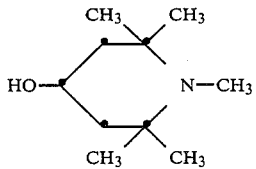
(a)

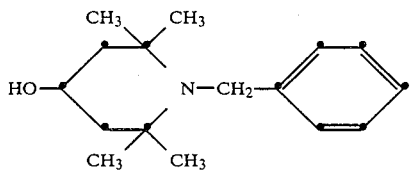
(b)

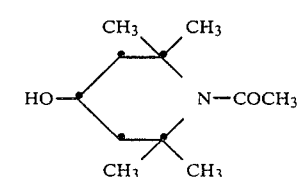
(c)

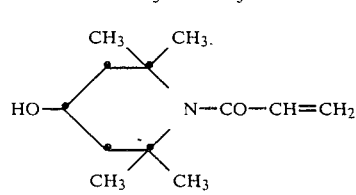
(d)

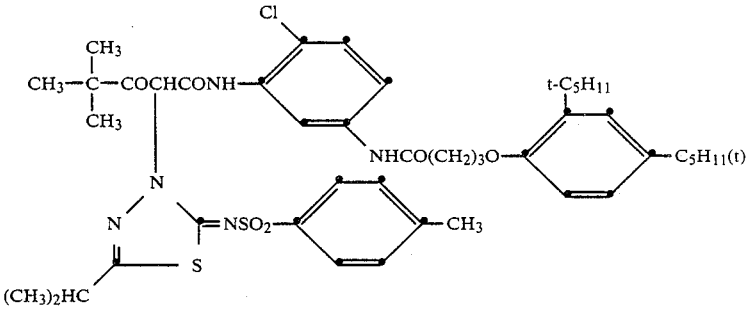

the corresponding stabilisers, to be used according to the invention, are obtained.

APPLICATION EXAMPLES 0.087 g of the yellow coupler of the formula and 0.026 g of one of the light stabilisers indicated in the tables which follow are dissolved in 2.0 ml of a tricresyl phosphate/ethyl acetate mixture (1.5 g in 100 ml). 7.0 ml of a 6% gelatine solution, 0.5 ml of an 8% solution of the wetting agent of the formula

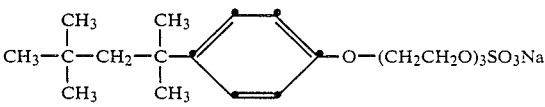

in isopropanol/water (3:4) and 0.5 ml of water are added to the above solution, and the mixture is ultrasonically emulsified at a power of 100 watt for 5 minutes.

2.0 ml of a silver bromide emulsion having a silver content of 6.0 g per liter, 0.7 ml of a 1% aqueous solution of the hardener of the formula

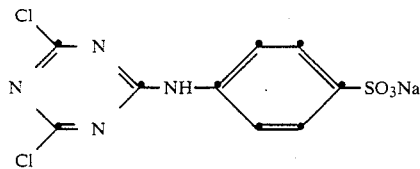

and 3.8 ml of water are added to 2.5 ml of the emulsion thus obtained, and the mixture is adjusted to a pH value of 6.5 and coated onto a subbed, plastis-coated white paper mounted on a glass plate.

After solidification, the plate with the emulsion is dried in a circulating air oven at room temperature.

After 7 days, samples cut to a size of 35×180 mm are exposed behind a step wedge with 3,00 lux x second and then processed by the Kodak Ektaprint 2 ® process.

The yellow wedges thus obtained are irradiated in an Atlas Weather-Ometer under a 2,500 W xenon lamp with a total of 42 kJoules/cm² ( a comparative sample does not contain any light stabiliser).

The resulting colour density loss is determined by measuring the colour density at $\lambda_{max.}$, using a TR 924A Densitometer ® from Messrs. Macbeth. The results are given in the table which follows:

| Light stabiliser No. | Percent loss of reflectance at the maximum |
|---|---|
| — | 36 |
| 14 | 16 |
| 40 | 21 |
| 42 | 21 |
| 47 | 15 |

What is claimed is:

1. A colour-photographic recording material which, in at least one light-sensitive silver halide emulsion layer, an interlayer and/or a protective layer, contains a light-stabilizing amount of at least one polyalkylpiperidine compound as a stabiliser, wherein the polyalkylpiperidine compound is of the formula I

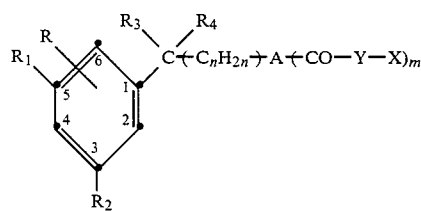

in which R is an OH group in the 2-position, 4-position or 6-position, $R_1$ is hydrogen, $C_1$-$C_4$-alkyl, a group of the formula II

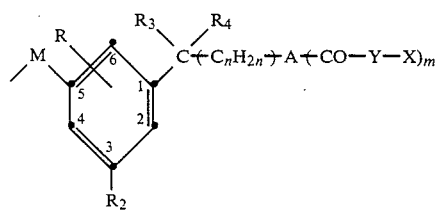

or a group of the formula III

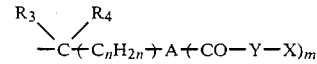

$R_2$ is $C_1$-$C_4$-alkyl, a group of the formula III or a group of the formula —CO—Y—X, $R_3$ and $R_4$ independently of one another are $C_1$-$C_8$-alkyl and, in addition, $R_4$ can, together with the group —($C_nH_{2n}$)—, form a $C_5$-$C_{12}$-cycloalkyl radical, n is a number from 1 to 20, m is 1 or 2, A is a direct C—C bond if m=1 or a radical $$-\overset{|}{\underset{|}{CH}}-$$

if m=2, Y is —O— or —N($R_5$)—, wherein $R_5$ is hydrogen, $C_1$-$C_{18}$-alkyl, $C_3$-$C_{12}$-alkenyl, $C_3$-$C_{12}$-cycloalkyl, phenyl, $C_7$-$C_{14}$-aralkyl, $C_7$-$C_{14}$-alkaryl, $C_2$-$C_{11}$-alkoxyalkyl or a group of the formula IV

M is a direct bond, —O—, —S—, —S—S—, —SO—, —SO$_2$— or a group —CH$_2$OCH$_2$—, —CH$_2$SCH$_2$—, —CH($R_8$)— or —N($R_9$)—, wherein $R_8$ is hydrogen, $C_1$-$C_{12}$-alkyl or $C_3$-$C_8$-alkyl or $C_3$-$C_8$-alkyl interrupted by 1-3 sulfur atoms, and $R_9$ is hydrogen, $C_1$-$C_{18}$-alkyl or unsubstituted or $C_1$-$C_4$-alkyl-substituted phenyl or benzyl, X is a group of the formula

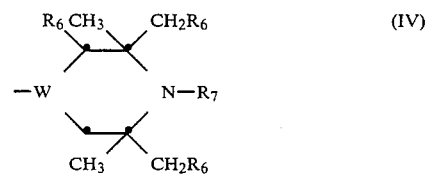

or of the formula

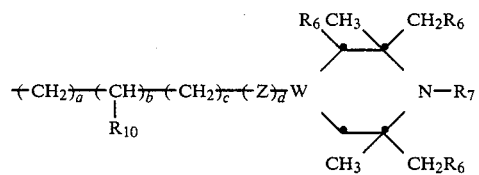

a is one of the numbers from 0 to 10, b, c and d independently of one another are the number 0 or 1, it being necessary for the sum a+b+c≠0 if d=1, $R_6$ is hydrogen or methyl, $R_7$ is hydroxyl, $C_1$-$C_{12}$-alkyl, $C_3$-$C_6$-alkenylmethyl, $C_3$-$C_4$-alkynylmethyl, $C_7$-$C_{14}$-aralkyl, glycidyl, $C_1$-$C_4$-alkyl substituted by halogen, cyano, —COOR$_{12}$ or —CON(R$_{13}$)—(R$_{14}$), a group —COR$_{15}$, —COOR$_{12}$, —CON(R$_{13}$) (R$_{14}$), —CH$_2$—CH(R$_{16}$)—OR$_{17}$, —SOR$_{18}$, —SO$_2$R$_{18}$, —OR$_{12}$ or —OCOR$_{15}$, $R_{12}$ being $C_1$-$C_{12}$-alkyl, alkyl, cyclohexyl or benzyl, $R_{13}$ being $C_1$-$C_{12}$-alkyl, alkyl, cyclohexyl, benzyl, phenyl or $C_7$-$C_{10}$-alkylphenyl, $R_{14}$ being hydrogen, $C_1$-$C_{12}$-alkyl, allyl, cyclohexyl or benzyl, or $R_{13}$ and $R_{14}$, together with the N atom to which they are attached, forming a 5-membered or 6-membered heterocyclic ring, $R_{15}$ being hydrogen, $C_1$–$C_{12}$-alkyl, $C_2$–$C_6$-alkenyl, chloromethyl, $C_5$–$C_8$-alkyl, $C_7$–$C_{14}$-aralkyl, phenyl, $C_7$–$C_{10}$-alkylphenyl or phenyl, phenylmethyl or phenylethyl which are substituted by 1 or 2 $C_1$–$C_4$-alkyls and 1 hydroxyl, $R_{16}$ being hydrogen, $C_1$–$C_4$-alkyl, $C_3$–$C_4$-alkoxyalkyl, phenyl or phenoxymethyl, $R_{17}$ being hydrogen, $C_1$–$C_{12}$-alkyl, a group —$COR_{15}$ or —$CON(R_{13})$ ($R_{14}$) or a group of the formula

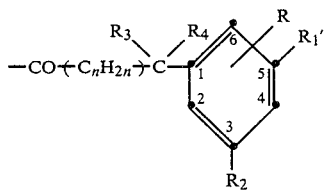

in which $R_1$ is hydrogen or $C_1$–$C_4$-alkyl, and $R_{18}$ being $C_1$–$C_{12}$-alkyl, phenyl or $C_7$–$C_{10}$-alkylphenyl, or $R_7$ is a group of the formula

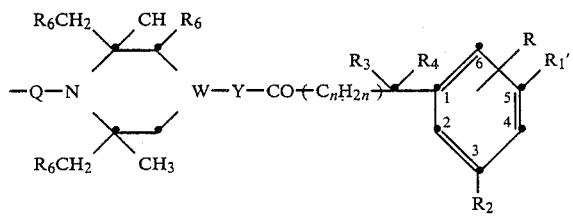

in which Q is a group —$(C_rH_{2r})$— wherein r is one of the numbers 2 to 12, or Q is $C_4$–$C_8$-alkylenylene, $C_5$–$C_{12}$-cycloalkylene, phenylene, xylylene, bitolylene or a group —CO—$(C_rH_{2r})$—CO—, Z is —O— or —$N(R_{19})$— wherein $R_{19}$ is hydrogen, $C_1$–$C_{18}$-alkyl, $C_3$–$C_{12}$-alkenyl, $C_3$–$C_{12}$-cycloalkyl, phenyl, $C_7$–$C_{14}$-alkaryl, $C_7$–$C_{14}$-aralkyl, $C_2$–$C_{11}$-alkoxyalkyl or a group —$COR_{20}$, —$COOR_{21}$, —$CON(R_{22})(R_{23})$, —$CH_2$—$CH(R_{24})$—$OR_{25}$, —$SOR_{26}$ or —$SO_2R_{26}$, $R_{20}$ having one of the meanings defined for $R_{15}$ or being a heterocyclic ring, $R_{21}$ having one of the meanings defined for $R_{12}$, $R_{22}$ having one of the meanings defined for $R_{13}$, $R_{23}$ having one of the meanings defined for $R_{14}$, $R_{24}$ having one of the meanings defined for $R_{16}$, $R_{25}$ having one of the meanings defined for $R_{17}$ and $R_{26}$ having one of the meanings defined for $R_{18}$, or $R_{19}$ is a group of the formula IV, $R_{10}$ is hydrogen, $C_1$–$C_{18}$-alkyl, $C_7$–$C_{23}$-phenoxyalkyl, phenyl, $C_7$–$C_{14}$-aralkyl, $C_2$–$C_{11}$-alkoxyalkyl or a group

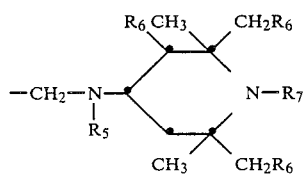

$R_{11}$ is hydrogen, —$OR_{27}$, —$OCOR_{28}$, —$N(R_{29})$—$COR_{28}$, —$OSO_2R_{28}$ and —$N(R_{29})$—$SO_2R_{28}$, $R_{27}$ being hydrogen, $C_1$–$C_{12}$-alkyl, allyl or benzyl, $R_{28}$ being hydrogen, $C_1$–$C_{12}$-alkyl, $C_2$–$C_6$-alkenyl, chloromethyl, $C_5$–$C_8$-cycloalkyl, $C_7$–$C_9$-phenylalkyl, $C_7$–$C_{10}$-alkylphenyl, phenyl or a group of the formula

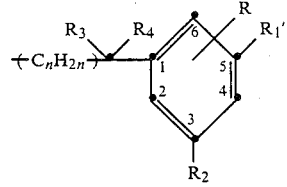

and $R_{29}$ being hydrogen, $C_1$–$C_{12}$-alkyl, $C_5$–$C_8$-cycloalkyl or benzyl, and W being one of the groups

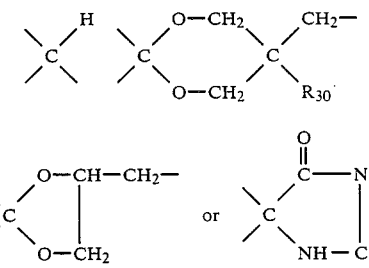

in which $R_{30}$ is methyl or ethyl, with the proviso that, if W is a cyclic ketal structure, d is 0 and the sum a+b+c must also be 0 and, if W is a hydantoin structure, d must be 0 and the sum a+b+c must be $\neq 0$, the repeatedly mentioned radicals and symbols always being as defined in the first instance and, with repeated occurrence of the group

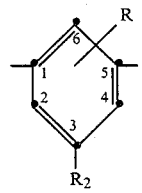

R always being in the same position.

2. A colour-photographic recording material according to claim 1, wherein each radical R in the compounds of the formula I is in the 6-position.

3. A colour-photographic recording material according to claim 1, wherein each radical R in the compounds of the formula I is in the 4-position.

4. A colour-photographic recording material according to claim 1, wherein each radical R in the compounds of the formula I is in the 2-position.

5. A colour-photographic recording material according to claim 1, which contains, as the stabiliser, at least one polyalkylpiperidine compound of the formula Ia

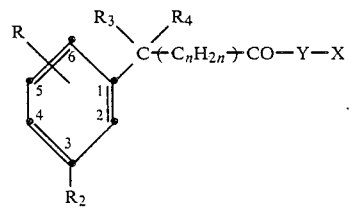

(Ia)

6. A colour-photographic recording material according to claim 1, which contains, as the stabiliser, at least one polyalkylpiperidine compound of the formula V

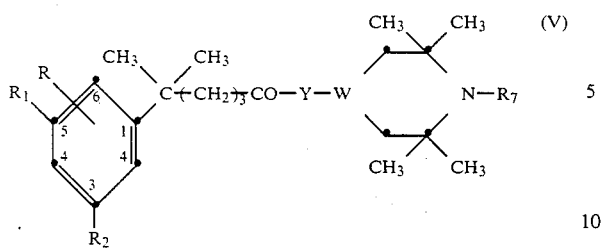

in which R is an OH group in the 2-position, 4-position or 6-position, $R_1$ is hydrogen, $C_1$-$C_{14}$-alkyl, a group of the formula VI

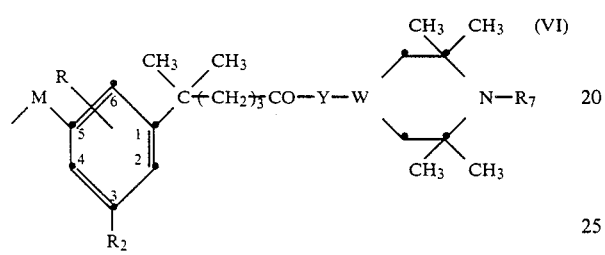

or a group of the formula VII

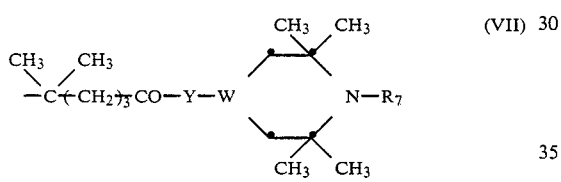

$R_2$ is $C_1$-$C_4$-alkyl or a group of the formula VII, Y is —O— or —N($R_5$)—, $R_5$ being hydrogen, $C_1$-$C_{12}$-alkyl, cyclohexyl, $C_3$-$C_4$-alkoxyalkyl or a group of the formula VIII

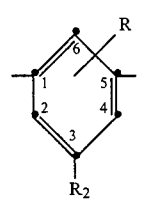

M is —CH($R_8$)— or —S—, $R_8$ being hydrogen or $C_1$-$C_4$-alkyl, $R_7$ is hydroxyl, methyl, allyl, benzyl, 2-hydroxyethyl, acetyl, acroyl or a group —CON($R_{13}$)($R_{14}$), wherein $R_{13}$ is $C_1$-$C_8$-alkyl, cyclohexyl or phenyl and $R_{14}$ is hydrogen, $C_1$-$C_8$-alkyl or cyclohexyl, or $R_7$ is a group of the formula

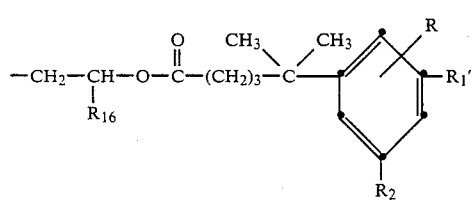

in which $R_{16}$ is hydrogen or methyl, and W is one of the groups

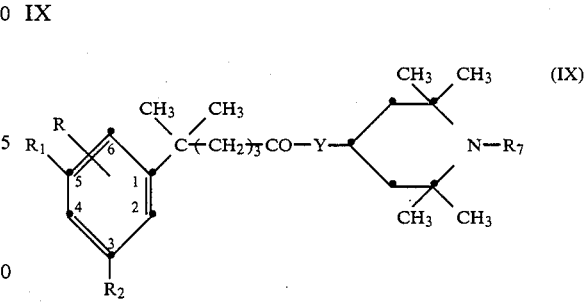

in which $R_{30}$ is methyl of ethyl, the radicals repeatedly mentioned in this claim always being as defined in this claim in the first instance and, with repeated occurrence of the group R always being in the same position.

7. A colour-photographic recording material according to claim 6, wherein each radical R in the compounds of the formula V is in the 6-position.

8. A colour-photographic recording material according to claim 6, wherein each radical R in the compounds of the formula V is in the 4-position.

9. A colour-photographic recording material according to claim 6, wherein each radical R in the compounds of the formula V is in the 2-position.

10. A colour-photographic recording material according to claim 1, which contains, as the stabiliser, at least one polyalkylpiperidine compound of the formula IX in which R is an OH group in the 2-position, 4-position or 6-position, $R_1$ is hydrogen, $C_1$-$C_4$-alkyl or a group of the formula X $R_2$ is $C_1$-$C_4$-alkyl or a group of the formula X, Y is —O— or —N($R_5$)—, wherein $R_5$ is hydrogen or $C_1$-$C_8$-alkyl, and $R_7$ hydroxyl, methyl, allyl, benzyl, 2-hydroxyethyl, acetyl, acryloyl or a group of the formula

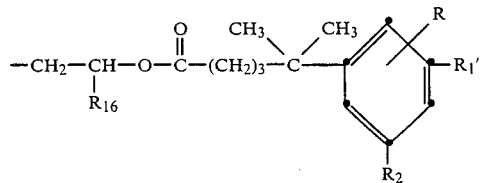

in which R₁₆ is hydrogen or methyl.

11. A colour-photographic recording material according to claim 10, wherein each radical R in the compounds of the formula IX is in the 6-position.

12. A colour-photographic recording material according to claim 10, wherein each radical R in the compounds of the formula IX is in the 4-position.

13. A colour-photographic recording material according to claim 10, wherein each radical R in the compounds of the formula IX is in the 2-position.

14. A colour-photographic recording material according to claim 1, which contains, as the stabiliser, a polyalkylpiperidine compound of the formula XVI

15. A colour-photographic recording material according to claim 1, which contains, as the stabiliser, a polyalkylpiperidine compound of the formula XVII

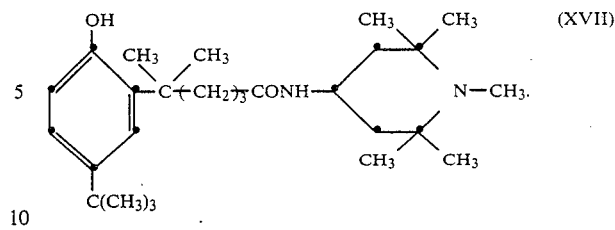

16. A colour-photographic recording material according to claim 1, which contains, as the stabiliser, a polyalkylpiperidine compound of the formula XVIII

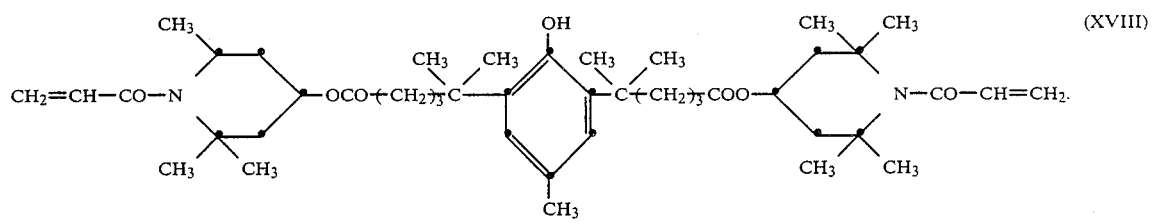

17. A colour-photographic recording material according to claim 1, which contains, as the stabiliser, a polyalkylpiperidine compound of the formula XIX (XIX)

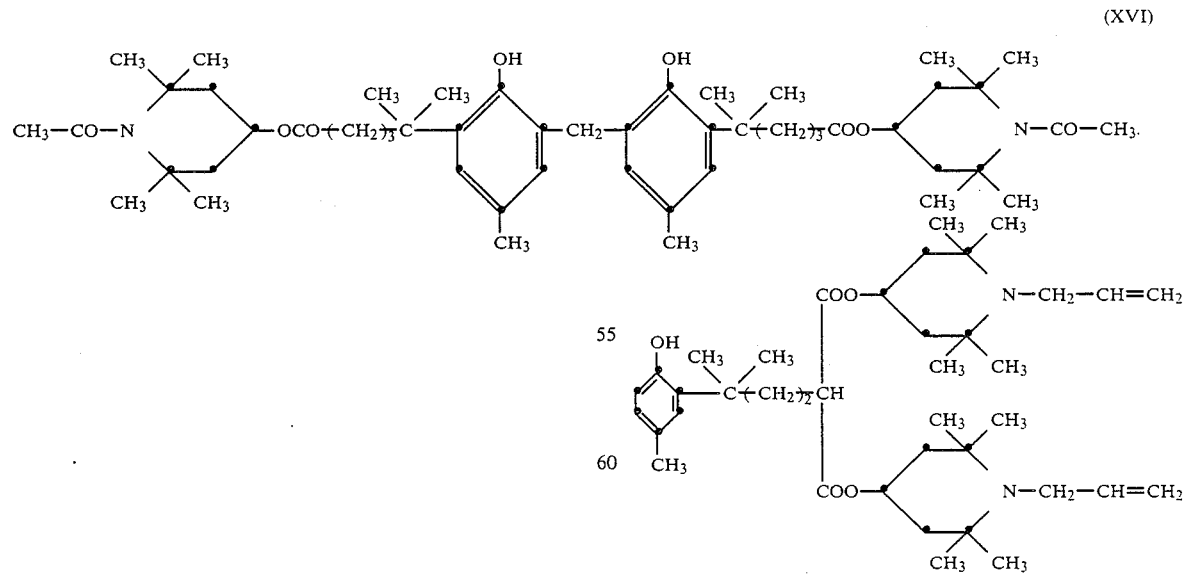

18. A colour-photographic recording material according to claim 1, which contains, as the stabiliser, a polyalkylpiperidine compound of the formula XX

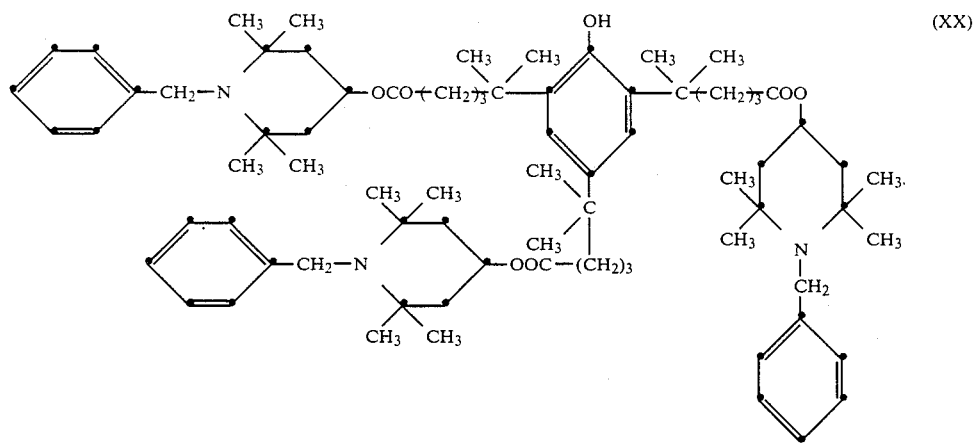

(XX)

19. A colour-photographic recording material according to claim 1, which contains a stabiliser of the formula I in combination with cyan, magenta and yellow couplers.

20. A colour-phtographic recording material according to claim 1, which contains a stabiliser of the formula I in combination with an ultraviolet absorber.

21. A colour-photographic recording material according to claim 20, wherein the ultraviolet absorber is a compound of the benzophenone, acrylonitrile, thiazolidone, benzotriazole, oxazole, thiazole or imidazol types.

22. A colour-photographic recording material according to claim 1, which contains the stabiliser of the formula I in combination with cyan, magenta and yellow couplers and with ultraviolet absorbers in the same layer.

23. A colour-photographic recording material according to claim 1, which contains 1 to 2,000 mg of the stabiliser of the formula I per $m^2$ of the layer into which it is incorporated.

24. A process for the production of photographic colour images by imagewise exposure and colour development of a colour-photographic recording material according to claim 1.

* * * * *